(12) United States Patent
Tsao et al.

(10) Patent No.: US 9,777,048 B2
(45) Date of Patent: Oct. 3, 2017

(54) USE OF PEDF-DERIVED POLYPEPTIDES FOR TREATING OSTEOARTHRITIS

(71) Applicants: Yeou-Ping Tsao, Taipei (TW);
Tsung-Chuan Ho, Taipei (TW)

(72) Inventors: Yeou-Ping Tsao, Taipei (TW);
Tsung-Chuan Ho, Taipei (TW)

(73) Assignee: MacKay Memorial Hospital, Taipei (TW)

( * ) Notice: Subject to any disclaimer, the term of this patent is extended or adjusted under 35 U.S.C. 154(b) by 0 days.

(21) Appl. No.: 14/429,693

(22) PCT Filed: Sep. 20, 2012

(86) PCT No.: PCT/CN2012/081659
§ 371 (c)(1),
(2) Date: Mar. 19, 2015

(87) PCT Pub. No.: WO2014/043871
PCT Pub. Date: Mar. 27, 2014

(65) Prior Publication Data
US 2015/0239942 A1    Aug. 27, 2015

(51) Int. Cl.
| | |
|---|---|
| *A61K 38/17* | (2006.01) |
| *C07K 14/47* | (2006.01) |
| *A61K 9/00* | (2006.01) |
| *A61P 19/02* | (2006.01) |
| *C07K 14/435* | (2006.01) |
| *A61K 38/57* | (2006.01) |
| *C07K 4/12* | (2006.01) |
| *A61K 38/00* | (2006.01) |

(52) U.S. Cl.
CPC .......... *C07K 14/435* (2013.01); *A61K 9/0019* (2013.01); *A61K 38/1709* (2013.01); *A61K 38/57* (2013.01); *C07K 4/12* (2013.01); *C07K 14/47* (2013.01); *A61K 38/00* (2013.01)

(58) Field of Classification Search
None
See application file for complete search history.

(56) References Cited

U.S. PATENT DOCUMENTS

2009/0069241 A1    3/2009    Barnstable et al.

FOREIGN PATENT DOCUMENTS

| CN | 102690344 A | 9/2012 |
|---|---|---|
| EP | 2508196 A1 | 10/2012 |
| JP | 2007-509984 A | 4/2007 |
| JP | 2009-538840 A | 11/2009 |
| WO | 2005/041887 A2 | 5/2005 |
| WO | 2006/054278 A2 | 5/2006 |
| WO | 2007/095350 A2 | 8/2007 |
| WO | 2007/137674 A1 | 12/2007 |
| WO | 2009/032477 A2 | 3/2009 |
| WO | 2014/023007 A1 | 2/2014 |
| WO | 2014/040302 A1 | 3/2014 |
| WO | 2014/043861 A1 | 3/2014 |

OTHER PUBLICATIONS

Mueller et al., Mol. Cancer Res., 2009, vol. 7(7):1078-1085.*
International Search Report issued in PCT/CN2012/081659 mailed on Jul. 11, 2013 (5 pages).
Extended European Search Report dated Apr. 15, 2016, issued by the European Patent Office in related European Patent Application No. EP-12884971.8 (8 pages).
Patent Examination Report No. 1 (Office Action) issued Jun. 30, 2016 by the Australian Patent Office in related Australian Patent Application No. 2012390210 (8 pages).
Official Action dated Oct. 27, 2016, issued by the Eurasian Patent Office in related Eurasian Patent Application No. EA-201590601/28, with English translation (2 pages).
Second Office Action dated Nov. 1, 2016, issued by the Japan Patent Office in related Japanese Patent Application No. JP 2015-532264, with Engllish translation (7 pages).
EPO Communication pursuant to Article 94(3) EPC (Office Action) dated Jan. 31, 2017, issued by the European Patent Office in related European Patent Application No. 12884971.8 (7 pages).
Office Action dated Feb. 23, 2016, issued by the Japan Patent Office in related Japanese Patent Application No. JP 2015-532264 (4 pages).
Hsieh, Jeng-Long, et al., "Intraarticular Gene Transfer of Thrombospondin-1 Suppresses the Disease Progression of Experimental Osteoarthritis"; Journal of Orthopaedic Research, Oct. 2010; vol. 28(10):1300-1306.
Mapp, P.I., et al., "Effects of a metalloproteinase inhibitor on osteochondral angiogenesis, chondropathy and pain behavior in a rat model of osteoarthritis"; Osteoarthritis and Cartilage, vol. 18 (2010); pp. 593-600.
Ashraf, S., et al., "Angiogenesis Inhibition has the Potential to Reduce Pain in the Rat Meniscal Injury Model of Osteoarthritis"; Angiogenesis & Synovial Tissue Biology No. 085, Osteoarthritis and Cartilage, vol. 18, Supplement 2 (2010); p. 545.
Pfander, D., et al., "Pigment epithelium derived factor—the product of the EPC-1 gene—is expressed by articular chondrocytes and up regulated in osteoarthritis"; Ann Rheum Dis vol. 65 (2006); pp. 965-967.
Notice of Grounds for Preliminary Rejection (Office Action) dated Jan. 16, 2017, issued by the Korean Intellectual Property Office (KIPO) in related Korean Patent Application No. KR 10-2015-7009725, with English Translation (8 pages).

(Continued)

*Primary Examiner* — Xiaozhen Xie
(74) *Attorney, Agent, or Firm* — Osha Liang LLP

(57) ABSTRACT

A method for treating osteoarthritis in a subject includes administering to a subject in need of such treatments a synthetic peptide, which has an amino acid sequence that has 20-39 amino acid residues. The synthetic peptide has at least 20 consecutive residues that has at least 90% amino acid sequence identity to residues 11-30 of SEQ ID NO: 1.

17 Claims, 4 Drawing Sheets

(56) References Cited

OTHER PUBLICATIONS

"Chapter 9 of Practical Medical Handbook", Edited by Chen Yancheng; published May 31, 2012; pp. 699-703 (27 pages).
First Office Action dated Feb. 24, 2017, issued by the State Intellectual Property Office of The Peoples Republic of China in corresponding Chinese Patent Application No. CN-201280077077.8, with USPTO Global Dossier English translation (11 pages).
Official Action dated Jun. 30, 2017, by the Eurasian Patent Office in related Eurasian Patent Application No. 201590601/28, with English translation (3 pages).

* cited by examiner

SEQUENCE LISTING

```
<160> NUMBER OF SEQ ID NOS: 15

<210> SEQ ID NO 1
<211> LENGTH: 39
<212> TYPE: PRT
<213> ORGANISM: Artificial Sequence
<220> FEATURE:
<223> OTHER INFORMATION: synthetic peptide

<400> SEQUENCE: 1

Leu Ser Val Ala Thr Ala Leu Ser Ala Leu Ser Leu Gly Ala Glu Gln
1               5                   10                  15

Arg Thr Glu Ser Ile Ile His Arg Ala Leu Tyr Tyr Asp Leu Ile Ser
            20                  25                  30

Ser Pro Asp Ile His Gly Thr
        35

<210> SEQ ID NO 2
<211> LENGTH: 34
<212> TYPE: PRT
<213> ORGANISM: Artificial Sequence
<220> FEATURE:
```

<223> OTHER INFORMATION: synthetic peptide

<400> SEQUENCE: 2

Ala Leu Ser Ala Leu Ser Leu Gly Ala Glu Gln Arg Thr Glu Ser Ile
1               5                   10                  15
Ile His Arg Ala Leu Tyr Tyr Asp Leu Ile Ser Ser Pro Asp Ile His
            20                  25                  30
Gly Thr

<210> SEQ ID NO 3
<211> LENGTH: 29
<212> TYPE: PRT
<213> ORGANISM: Artificial Sequence
<220> FEATURE:
<223> OTHER INFORMATION: synthetic peptide

<400> SEQUENCE: 3

Ser Leu Gly Ala Glu Gln Arg Thr Glu Ser Ile Ile His Arg Ala Leu
1               5                   10                  15
Tyr Tyr Asp Leu Ile Ser Ser Pro Asp Ile His Gly Thr
            20                  25

<210> SEQ ID NO 4
<211> LENGTH: 25
<212> TYPE: PRT
<213> ORGANISM: Artificial Sequence
<220> FEATURE:
<223> OTHER INFORMATION: synthetic peptide

<400> SEQUENCE: 4

Glu Gln Arg Thr Glu Ser Ile Ile His Arg Ala Leu Tyr Tyr Asp Leu
1               5                   10                  15
Ile Ser Ser Pro Asp Ile His Gly Thr
            20                  25

<210> SEQ ID NO 5
<211> LENGTH: 24
<212> TYPE: PRT
<213> ORGANISM: Artificial Sequence
<220> FEATURE:
<223> OTHER INFORMATION: synthetic peptide

<400> SEQUENCE: 5

Ser Leu Gly Ala Glu Gln Arg Thr Glu Ser Ile Ile His Arg Ala Leu
1               5                   10                  15
Tyr Tyr Asp Leu Ile Ser Ser Pro
            20

<210> SEQ ID NO 6
<211> LENGTH: 20
<212> TYPE: PRT
<213> ORGANISM: Artificial Sequence
<220> FEATURE:
<223> OTHER INFORMATION: synthetic peptide

<400> SEQUENCE: 6

Ser Leu Gly Ala Glu Gln Arg Thr Glu Ser Ile Ile His Arg Ala Leu
1               5                   10                  15
Tyr Tyr Asp Leu
            20

<210> SEQ ID NO 7
<211> LENGTH: 18

```
<212> TYPE: PRT
<213> ORGANISM: Artificial Sequence
<220> FEATURE:
<223> OTHER INFORMATION: synthetic peptide

<400> SEQUENCE: 7

Glu Gln Arg Thr Glu Ser Ile Ile His Arg Ala Leu Tyr Tyr Asp Leu
1               5                   10                  15

Ile Ser

<210> SEQ ID NO 8
<211> LENGTH: 29
<212> TYPE: PRT
<213> ORGANISM: Artificial Sequence
<220> FEATURE:
<223> OTHER INFORMATION: synthetic peptide

<400> SEQUENCE: 8

Ser Leu Gly Ala Glu His Arg Thr Glu Ser Val Ile His Arg Ala Leu
1               5                   10                  15

Tyr Tyr Asp Leu Ile Thr Asn Pro Asp Ile His Ser Thr
            20                  25

<210> SEQ ID NO 9
<211> LENGTH: 20
<212> TYPE: PRT
<213> ORGANISM: Artificial Sequence
<220> FEATURE:
<223> OTHER INFORMATION: synthetic peptide

<400> SEQUENCE: 9

Ser Leu Gly Ala Glu His Arg Thr Glu Ser Val Ile His Arg Ala Leu
1               5                   10                  15

Tyr Tyr Asp Leu
            20

<210> SEQ ID NO 10
<211> LENGTH: 44
<212> TYPE: PRT
<213> ORGANISM: Artificial Sequence
<220> FEATURE:
<223> OTHER INFORMATION: synthetic peptide

<400> SEQUENCE: 10

Val Leu Leu Ser Pro Leu Ser Val Ala Thr Ala Leu Ser Ala Leu Ser
1               5                   10                  15

Leu Gly Ala Glu Gln Arg Thr Glu Ser Ile Ile His Arg Ala Leu Tyr
            20                  25                  30

Tyr Asp Leu Ile Ser Ser Pro Asp Ile His Gly Thr
        35                  40

<210> SEQ ID NO 11
<211> LENGTH: 418
<212> TYPE: PRT
<213> ORGANISM: Homo sapiens

<400> SEQUENCE: 11

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45
```

Val Pro Val Asn Lys Leu Ala Ala Val Ser Asn Phe Gly Tyr Asp
 50                  55                  60

Leu Tyr Arg Val Arg Ser Thr Ser Pro Thr Asn Val Leu Leu
65                  70                  75                  80

Ser Pro Leu Ser Val Ala Thr Ala Leu Ser Ala Leu Ser Leu Gly Ala
                 85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
            115                 120                 125

Val Thr Ala Pro Gln Lys Asn Leu Lys Ser Ala Ser Arg Ile Val Phe
            130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
            195                 200                 205

Gly Val Ala His Phe Lys Gly Gln Trp Val Thr Lys Phe Asp Ser Arg
210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
            355                 360                 365

Ala Gly Thr Thr Pro Ser Pro Gly Leu Gln Pro Ala His Leu Thr Phe
370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 12
<211> LENGTH: 20
<212> TYPE: DNA
<213> ORGANISM: Artificial Sequence
<220> FEATURE:
<223> OTHER INFORMATION: Synthetic

```
<400> SEQUENCE: 12
ttggaaatcc agaaccttcg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gtccagtgtg tagcgtgtgg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
agacagccgc atcttcttgt                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
cttgccgtgg gtagagtcat                                              20
```

USE OF PEDF-DERIVED POLYPEPTIDES FOR TREATING OSTEOARTHRITIS

CROSS REFERENCE TO RELATED APPLICATIONS

This is a national phase application based on PCT/CN2012/081659, filed on Sep. 20, 2012, the disclosure of which is incorporated by reference in its entirety.

BACKGROUND OF THE INVENTION

1. Field of the Invention

The present disclosure relates to the treatment of osteoarthritis. In particular, the disclosed invention relates to the use of PEDF-derived polypeptides for treating osteoarthritis.

2. Description of Related Art

Osteoarthritis is a degenerative joint disease, which mostly affects cartilage, the slippery tissue that covers the ends of bones where they meet to form a joint. Healthy cartilage allows bones to glide over one another and absorbs energy from the shock of physical movement. In osteoarthritis, the surface layer of cartilage breaks and wears away, and therefore, bones under the damaged cartilages rub together, causing pain, swelling, and loss of motion of the joint. Osteoarthritis is associated with aging and will most likely affect the joints that have been continually stressed throughout the years including the knees, hips, fingers, and lower spine region.

Osteoarthritis is by far the most common type of arthritis. As of 2008, an estimated 27 million Americans age 25 and older have osteoarthritis. Worldwide estimates are that 9.6% of men and 18.0% of women aged over 60 years have symptomatic osteoarthritis. World Health Organization (WHO) survey indicates that 80% of those with osteoarthritis will have limitations in movement, and 25% cannot perform their major daily activities of life.

There is no cure for osteoarthritis. Current disease management centers on controlling joint pain and stiffness and preserving the patient's ability to go about everyday activities. Physical therapy is often advised because it helps strengthen muscles and bones, increase muscle flexibility, and thereby reduce the pain. Medications for osteoarthritis mostly center in pain relief. Analgesics and topical pain relievers combat discomfort, but don't fight inflammation. Oral and injectable corticosteroids control inflammation, but aren't recommended for frequent or long-term use. Non-steroidal anti-inflammatory drugs (NSAIDs) are prescribed to reduce pain, swelling and inflammation; however, they can cause stomach distress and ulcers, as well as increase the risk of heart attack in some people. Surgery ranging from arthroscopic procedures to total joint arthroplasty may be an option for extremely damaged joints.

In view of the foregoing, there remains a need in the art for means that effectively treats osteoarthritis.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based, at least, on the finding that synthetic peptides derived from pigment epithelium-derived factor (PEDF) may stimulate the proliferation of chondrocytes, promote the regeneration of cartilages, and induce the chondrogenesis of mesenchymal stem cells, and hence they are effective in treating osteoarthritis in a subject. The PEDF-derived synthetic peptides of this invention are, therefore, useful as a medicament for treating osteoarthritis.

Accordingly, in one aspect, the present disclosure is directed to a use of a synthetic peptide for treating osteoarthritis in a subject.

According to embodiments of the present disclosure, the synthetic peptide is 20-39 amino acid residues in length, and has an amino acid sequence that is at least 80% identical to SEQ ID NO: 1. Also, the amino acid sequence comprises at least 20 consecutive residues, which is at least 90% identical to residues 11-30 of SEQ ID NO: 1, such that the synthetic peptide is useful in treating osteoarthritis in a subject.

According to optional embodiments of the present disclosure, at least 4 consecutive residues of the synthetic peptide are identical to residues 11-14 of SEQ ID NO: 1. Non-limiting examples of such synthetic peptides include those respectively having an amino acid sequence of SEQ ID NO: 1 (39-mer), SEQ ID NO: 2 (34-mer), SEQ ID NO: 3 (29-mer), SEQ ID NO: 5 (24-mer), SEQ ID NO: 6 (20-mer), SEQ ID NO: 8 (MO 29-mer), and SEQ ID NO: 9 (MO 20-mer). In some embodiments of the present disclosure, the amino acid sequence of the synthetic peptide is SEQ ID NO: 3 (29-mer), SEQ ID NO: 5 (24-mer), or SEQ ID NO: 6 (20-mer).

According to various embodiments of the present disclosure, the subject may be any animal classified as a mammal, including human.

In another aspect, the present disclosure is directed to a pharmaceutical composition for treating osteoarthritis in a subject. The subject may be any animal classified as a mammal, including human.

According to one embodiment of the present disclosure, the pharmaceutical composition comprises a synthetic peptide according to any of the above-mentioned aspect/embodiments, and the synthetic peptide is present in an effective amount sufficient to treat osteoarthritis in the subject. The pharmaceutical composition also comprises a pharmaceutically acceptable excipient for the synthetic peptide.

In certain optional embodiments, the pharmaceutical composition further comprises a glycosaminoglycan, such as hyaluronic acid or sodium hyaluronate.

In various embodiments of the present disclosure, the pharmaceutical composition may be formulated into an injectable dosage form.

In yet another aspect, the present invention is directed to a method for treating osteoarthritis in a subject that has at least one lesion suffering from osteoarthritis. The subject may be any animal classified as a mammal, including human.

In one embodiment, the method comprises administering to the subject an effective amount of the synthetic peptide according to any of the above-mentioned aspect/embodiments. In particular, the synthetic peptide is administered in such a way that the synthetic peptide would reach the synovial cavity of the subject so as to treat osteoarthritis.

According to optional embodiments, the synthetic peptide is formulated into a pharmaceutical composition according to the above-mentioned aspect/embodiments of the present disclosure.

In some optional embodiments, the synthetic peptide or the pharmaceutical composition is intra-articularly injected into the synovial cavity of the subject.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1:
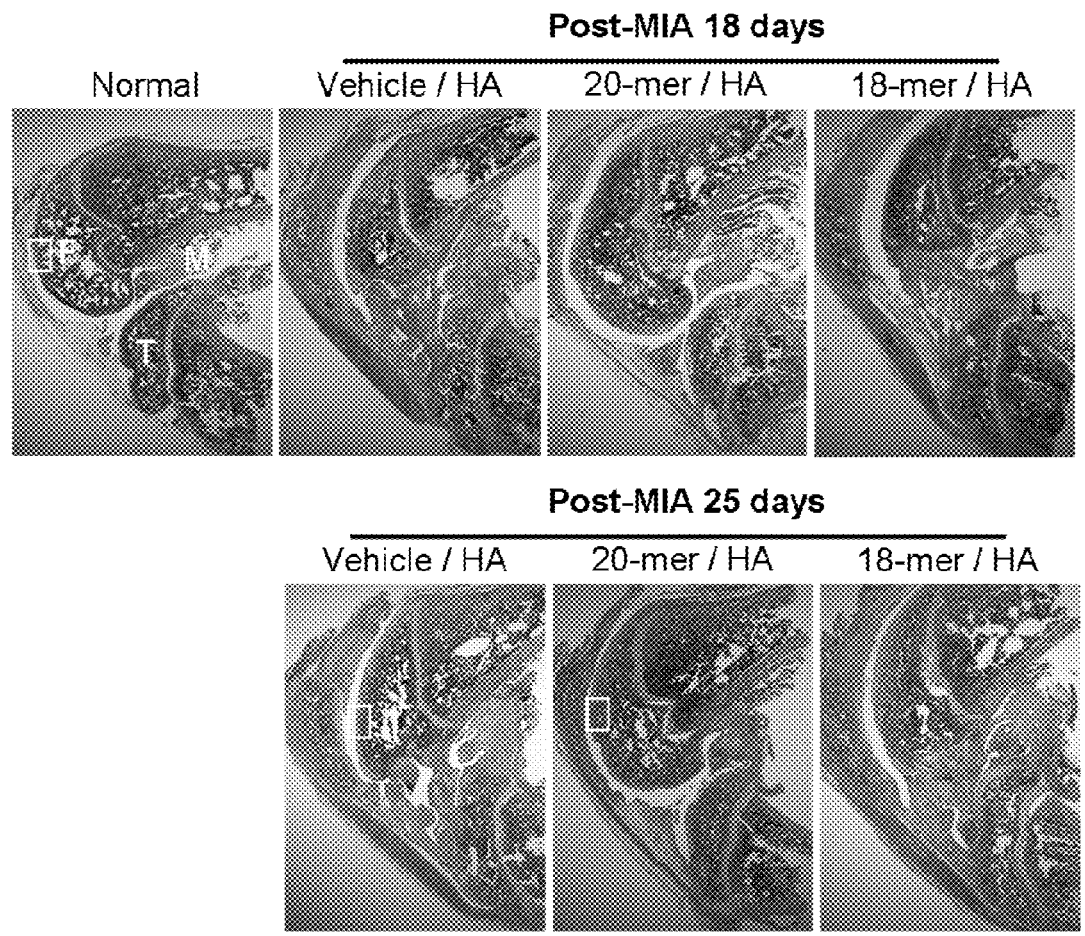
FIG. 1 provides representative H&E stained sections of knee joint specimens according to one working example of the present disclosure (F: femoral condyle; T: tibial condyle, M: meniscus)

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the entire application (including the specification, examples, and appended claims) are collected here. Unless otherwise defined herein, scientific and technical terminologies employed in the present disclosure shall have the meanings that are commonly understood and used by one of ordinary skill in the related art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "peptide" denotes a polymer of amino acid residues. By the term "synthetic peptide" as used herein, it is meant a peptide that does not comprise an entire naturally occurring protein molecule. The peptide is "synthetic" in that it may be produced by human intervention using such techniques as chemical synthesis, recombinant genetic techniques, or fragmentation of the whole protein or the like. Throughout the present disclosure, the positions of any specified amino acid residues within a peptide are numbered starting from the N terminus of the peptide.

As used herein, "proliferating" and "proliferation" refers to an increase in the number of cells in a population by means of cell division.

"Percentage (%) amino acid sequence identity" with respect to the synthetic polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The terms "treatment" and "treating" are used herein to include preventative (e.g., prophylactic), curative, or palliative treatment that results in a desired pharmaceutical and/or physiological effect. Preferably, the effect is therapeutic in terms of partially or completely curing osteoarthritis. In particular, the term "treating" to application or administration of the physical and/or chemical intervention to a subject, who has a medical condition, a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. According to principles and spirits of the present disclosure, said disease, disorder, or condition is osteoarthritis. Treatment is generally "effective" if one or more symptoms or clinical markers are reduced as that term is defined herein.

The term "effective amount" as used herein refers to the quantity of a component which is sufficient to yield a desired response. The specific effective amount will vary with such factors as the particular condition being treated, the physical condition of the subject (e.g., the subject's body mass, age, or gender), the type of mammal or animal being treated, the duration of the treatment, the nature of concurrent therapy (if any), and the specific formulations employed. An effective amount is also one in which any toxic or detrimental effects of the compound or composition are outweighed by the therapeutically beneficial effects.

The terms "application" or "administration" are used interchangeably herein to refer means providing a synthetic peptide or a pharmaceutical composition of the present invention to a subject to treat osteoarthritis. According to various embodiments of the present disclosure, intra-articular injection is a preferred delivery route. For example, the synthetic peptide or pharmaceutical composition of the present invention is intra-articularly injected into the synovial cavity of the subject so as to promote cartilage regeneration, thereby treating osteoarthritis.

The term "excipient" as used herein means any inert substance (such as a powder or liquid) that forms a vehicle/carrier for the synthetic PEDF peptide(s) of the present disclosure. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

As used herein, a "pharmaceutically acceptable" component is one that is suitable for use with humans and/or animals without undue adverse side effects (such as toxicity, irritation, and allergic response) commensurate with a reasonable benefit/risk ratio. Also, each excipient must be "acceptable" in the sense of being compatible with the other ingredients of the pharmaceutical formulation. The carrier can be in the form of a solid, semi-solid, or liquid diluent, cream or a capsule.

The term "subject" refers to a mammal including the human species that is treatable with the synthetic peptides, compositions, and/or methods of the present invention. The term "subject" is intended to refer to both the male and female gender unless one gender is specifically indicated.

Pigment epithelium-derived factor (PEDF) is a multifunctional secreted protein that has anti-angiogenic, anti-tumorigenic, and neurotrophic functions. Human PEDF protein (SEQ ID NO: 11) is a secreted protein of roughly 50 kDa size and 418 amino acids in length. A 34-mer fragment (residues 44-77) and a 44-mer fragment (residues 78-121; SEQ ID NO: 10) of PEDF have been identified to have anti-angiogenic and neurotrophic properties, respectively.

The present disclosure is based, at least, on the finding that synthetic peptides derived from the 44-mer PEDF may promote the cartilage regeneration via a variety of mechanisms. Examples of the present disclosure demonstrate that the present synthetic peptides may increase the proliferation of chondrocytes and induce the chondrogenesis of mesenchymal stem cells. Another inventive feature of the present invention lies in that the synthetic peptides are much shorter (20-39 amino acid residues) than the full-length PEDF and thus overcomes the limitations associated with the clinical use of conventional protein drugs, including high manufacturing cost, low bioavailability, and poor pharmacokinetics. Accordingly, the present synthetic peptides are useful for treating osteoarthritis.

Thus, in one aspect, the present disclosure is directed to a use of a synthetic peptide for treating osteoarthritis in a subject.

According to embodiments of the present disclosure, the synthetic peptide has 20-39 amino acid residues in length, and has at least 80% amino acid sequence identity with the amino acid sequence of LSVATALSALSLGAEQRTESI-IHRALYYDLISSPDIHGT (SEQ ID NO: 1). For example, the synthetic peptide may have an amino acid sequence identity of about 80, 81, 82, 83, 84, 85, 86, 87, 88, 89, 90, 91, 92, 93, 94, 95, 96, 97, 98, 99, or 100 percent with SEQ ID NO: 1. Also, the synthetic peptide comprises at least 20 consecutive residues that are at least 90% identical to residues 11-30 of SEQ ID NO: 1. Specifically, the 20 consecutive amino acid residues may have about 90, 91, 92, 93, 94, 95, 96, 97, 98, 99, or 100 percent amino acid sequence identity with residues 11-30 of SEQ ID NO: 1.

In one embodiment, the synthetic peptide has the sequence of SEQ ID NO: 1, which has 39 amino acids in length. This synthetic peptide is referred to as 39-mer in the description hereinbelow. This 39-mer peptide corresponds to residues 83-121 of human PEDF and hence is a short variant derived from the known PEDF 44-mer (corresponding to residues 78-121 of PEDF).

Prior experiments conducted by the present inventors, such as those disclosed in the co-pending U.S. application Ser. No. 13/428,996 (the entirety of which is incorporated herein by reference) and experiments provided hereinbelow, reveal that several short, synthetic PEDF peptides derived from the 39-mer, are capable of treating osteoarthritis in a subject.

For example, based on experiments disclosed in both the prior application and the present application, a 34-mer synthetic peptide having the sequence of ALSALSL-GAEQRTESIIHRALYYDLISSPDIHGT (SEQ ID NO: 2) is effective in treating osteoarthritis in a subject. This 34-mer peptide corresponds to residues 88-121 of human PEDF. According to the process for estimating percentage of sequence identity between any two given sequences provided above, the 34-mer has a 100% amino acid sequence identity to the 39-mer, and the $6^{th}$-$25^{th}$ amino acid residues of the 34-mer has a 100% amino acid sequence identity to the amino acid residues 11-30 of the 39-mer.

Additionally, according to various examples hereinbelow, a 29-mer synthetic peptide having the sequence of SLGAEQRTESIIHRALYYDLISSPDIHGT (SEQ ID NO: 3) has been confirmed to be effective in treating osteoarthritis in a subject. This 29-mer peptide corresponds to residues 93-121 of human PEDF with a 100% amino acid sequence identity to the 39-mer. Also, the $1^{st}$-$20^{th}$ amino acid residues of the 29-mer has a 100% amino acid sequence identity to the amino acid residues 11-30 of the 39-mer.

In some examples, a 24-mer has been confirmed to be effective in treating osteoarthritis in a subject. The 24-mer has the sequence of SLGAEQRTESIIHRALYYDLISSP (SEQ ID NO: 5), which corresponds to residues 93-116 of human PEDF. This 24-mer peptide has a 100% amino acid sequence identity to the 39-mer in which the first twenty amino acid residues thereof has a 100% amino acid sequence identity to the amino acid residues 11-30 of the 39-mer.

In other examples, it has been established that a 20-mer may treat osteoarthritis in a subject. The 20-mer has the sequence of SLGAEQRTESIIHRALYYDL (SEQ ID NO: 6), which corresponds to residues 93-112 of human PEDF. This 20-mer peptide is completely identical to the amino acid residues 11-30 of the 39-mer (100% amino acid sequence identity), and has a 100% amino acid sequence identity to the 39-mer.

Two synthetic peptides derived from mouse PEDF may also treat osteoarthritis in a subject based on experiments disclosed in both the prior application and the present application. The first mouse-derived peptide is referred to as "Mo 29-mer" in the present disclosure. The Mo 29-mer has a sequence of SLGAEHRTESVIHRALYYDLITNPDIHST (SEQ ID NO: 8), which has a 83% amino acid sequence identity to 39-mer, and the first 20 amino acid residues thereof has a 90% amino acid sequence identity to the 11-30 amino acid residues of the 39-mer. Another mouse-derived peptide, Mo 20-mer has a sequence of SLGAEHRTESVIHRALYYDL (SEQ ID NO: 9). The Mo 20-mer has a 90% amino acid sequence identity to either the 39-mer or the 11-30 amino acid residues of the 39-mer.

Optionally, the synthetic peptide comprises 4 consecutive residues identical to residues 11-14 of SEQ ID NO: 1. It is believed that residues 11-14 (i.e., SLGA) of SEQ ID NO: 1 play an important role in maintaining the biological function of the short PEDF peptides of the present invention. For example, according to various examples provided below, an 18-mer peptide (EQRTESIIHRALYYDLIS; SEQ ID NO: 7), which lacks the SLGA residues, fails to elicit any protection against osteoarthritis in a subject. Also, based on experiments disclosed in both the prior application and the present application, a 25-mer peptide (EQRTESIIHRALYYDLISSPDIHGT; SEQ ID NO: 4), which also lacks the SLGA residues, is ineffective in treating osteoarthritis in a subject.

The synthetic Peptides of the invention can be synthesized by commonly used methods such as t-BOC or FMOC protection of alpha-amino groups. Both methods involve stepwise syntheses whereby a single amino acid is added at each step starting from the C terminus of the peptide. Peptides of the present invention can also be synthesized by the well-known solid phase peptide synthesis methods.

Other synthetic peptides with conservative variation with respect to the 39-mer are also contemplated. The term "conservative variation" as used herein denotes the replacement of an amino acid residue by another, biologically similar residue. Examples of conservative variations include the substitution of one hydrophobic residue such as isoleucine, valine, leucine, or methionine for one another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

According to various embodiments of the present disclosure, the subject may be any animal classified as a mammal, including human.

The synthetic peptides according to above-mentioned embodiments may be formulated into pharmaceutical compositions for treating osteoarthritis in a subject, which falls within other aspects of the present disclosure.

According to one embodiment of the present disclosure, the pharmaceutical composition comprises a synthetic peptide according to any of the above-mentioned aspect/embodiments, and the synthetic peptide is present in an effective amount sufficient to treat osteoarthritis in the subject. The pharmaceutical composition also comprises a pharmaceutically acceptable excipient for the synthetic peptide.

According to optional embodiments of the present disclosure, the synthetic peptide is present in the pharmaceutical composition in an amount of about 1-1,000 µM; preferably, about 10-500 µM; and more preferably, about 25-250 µM. For example, the concentration of the synthetic peptides may be about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 1,000 µM. Specifically, the concentration used in the working example below on rats (weighing about 310 grams) is about 200 µM. Persons having ordinary skills could calculate the human equivalent dose (HEQ) for the present synthetic peptide or pharmaceutical composition based on the animal doses provided herein. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The pharmaceutical composition is prepared in accordance with acceptable pharmaceutical procedures, such as described in Remington's Pharmaceutical Sciences, $17^{th}$ edition, ed. Alfonoso R. Gennaro, Mack Publishing Company, Easton, Pa. (1985).

The choice of a pharmaceutically acceptable excipient to be used in conjunction with a synthetic peptide is basically determined by the way the pharmaceutical composition is to be administered.

According to one optional embodiment of the present disclosure, the pharmaceutical composition may be administered locally via intra-articular injection. In this case, the synthetic peptide may be formulated with a pharmaceutically acceptable excipient such as a sterile aqueous solution, which is preferably isotonic with the body fluid of the recipient. Such formulations may be prepared by dissolving or suspending the solid active ingredient in water containing physiologically compatible substances such as sodium chloride, glycine, and the like, and having a buffered pH compatible with physiological conditions to produce an aqueous solution, and rendering said solution sterile. Other diluents or solvent suitable for manufacturing sterile injectable solution or suspension include, but are not limited to, 1,3-butanediol, mannitol, water, and Ringer's solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

According to optional embodiment of the present invention, the pharmaceutical composition may further comprise glycosaminoglycan. Glycosaminoglycans are linear polysaccharides composed of repeating disaccharide units with a carboxyl group and one or more sulfates. Glycosaminoglycans are attached to core proteins to form proteoglycans which are the major components of bone extracellular matrix. In cartilage suffering from osteoarthritis, the amount of glycosaminoglycans in the matrix is reduced, and the binding between glycosaminoglycans and type II collagen is decreased, which may incur further damage to the lesion. Therefore, providing exogenous glycosaminoglycans to the lesion may facilitate the treatment of osteoarthritis. Examples of glycosaminoglycans include, but are not limited to, hyaluronic acid and sodium hyaluronate. As one non-limiting example, the pharmaceutical composition of the present invention may comprise 1-15% (wt %) of hyaluronic acid.

Still optionally, pharmaceutical compositions of the present invention can also comprise various pharmaceutically-acceptable additives well known to the art. Said additives include, but are not limited to, drying agent, anti-itch agents, anti-foaming agents, buffers, neutralizing agents, pH adjusting agents, coloring agents, discoloring agents, emollients, emulsifying agents, emulsion stabilizers, viscosity builders, humectants, odorants, preservatives, antioxidants, chemical stabilizers, thickening agents, stiffening agents, or suspending agents.

In yet another aspect, the present invention is directed to a method for treating osteoarthritis in a subject. The subject may be any animal classified as a mammal, including human. According to principles and spirits of the present disclosure, the method promotes cartilage regeneration which in turn ameliorates or cures osteoarthritis in the subject.

In one embodiment, the method comprises administering to the subject an effective amount of the synthetic peptide according to any of the above-mentioned aspect/embodiments such that the synthetic peptide reaches the synovial cavity in proximity to the lesion.

According to optional embodiments, the synthetic peptide is formulated into a pharmaceutical composition according to the above-mentioned aspect/embodiments of the present disclosure.

In some optional embodiments, the synthetic peptide or the pharmaceutical composition is intra-articularly injected into the synovial cavity.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods
Materials
Dulbecco's modified Eagle's medium (DMEM), fetal bovine serum (FBS), 0.25% trypsin, antibiotics, TRIzol, and Dynabeads were purchased from Invitrogen (Carlsbad, Calif.). Hyaluronic acid (HA), mono-iodoacetate (MIA), dimethyl sulfoxide (DMSO), fibronectin, Percoll, insulin, hydrocortisone, bovine serum albumin (BSA), 5-bromo-2'-deoxyuridine (BrdU), Hoechst 33258 dye were all from Sigma-Aldrich (St. Louis, Mo.). Anti-BrdU, anti-aggrecan, and anti-type 2 collagen antibodies were from GeneTex (Taipei, Taiwan). All fluorescent dye-conjugated secondary antibodies were purchased from BioLegend (San Diego, Calif.). Pronase and collagenase were obtained from Roche (Indianapolis, Ind.), Hematoxylin and eosin (H&E) dyes were purchased from Merck (Rayway, N.J., USA).

Synthetic PEDF peptides, including 29-mer (SEQ ID NO: 3), 24-mer (SEQ ID NO: 5), 20-mer (SEQ ID NO: 6), and 18-mer (SEQ ID NO: 7) were synthesized and modified by acetylation at the $NH_2$ termini and amidation at the COOH termini. The modified peptide were subsequently characterized by mass spectrometry (>95% purity) (GenScript (Piscataway, N.J.)). Each PEDF-derived short synthetic peptide (the 29-mer, 24-mer, or 20-mer; herein below, PEDF peptide) was reconstituted in DMSO as stock (5 mM), and stored at −20° C. for further use.

Animals
All animals used in working examples of the present disclosure were housed in an animal room under temperature control (24-25° C.) and 12:12 light-dark cycle. Standard laboratory chow and tap water were available ad libitum. The experiments procedures were approved by the Mackay Memorial Hospital Review Board (New Taipei City, Taiwan, R.O.C.) and were performed in compliance with national animal welfare regulations.

Animal models of osteoarthritis were established by intra-articular injection of MIA. Specifically, adult 10-wk-old male Sprague-Dawley rats (initial body wt=312±11 g) were anesthetized with an intraperitoneal injection of xylazine (10 mg/kg), followed by a single intra-articular injection of MIA (1 mg of MIA in 25 µl of sterile saline) in the right knee. In particular, the MIA solution was injected through the patellar ligament by using a 27G needle with the leg flexed at a 90° angle at the knee.

For the detection of in vivo cell proliferation, BrdU was reconstituted in DMSO as stock (80 mM). 150 µl of BrdU mixed with 350 µl of PBS was intraperitoneally injected into rat at 16 hours prior to euthanasia. DNA synthesis was then assessed by BrdU labeling with anti-BrdU antibodies according to procedures set forth below.

Isolation and Culture of Articular Chondrocytes
Articular cartilage was harvested from femoral condyles (the anterior, posterior and lateral areas) of adult 8-wk-old male Sprague-Dawley rats. Care was taken to avoid contamination with synovium and to disruption of the bony structures during the sampling process. Dissected tissue was cut into small (about 0.5 $mm^3$) pieces and digested sequentially by pronase (70 U/ml, 1 hour at 37° C.) and collagenase (300 U/ml, 3 hours at 37° C.). After digestion, collagenase was removed by a single wash in sterile phosphate-buffered saline (PBS), followed by two further washes in DMEM supplemented with 2% FBS. For primary culture, 6000 trypan blue-negative cells per well were plated on 10 µg/ml fibronectin-coated coverslips in a 6-well plate in 10% FBS-DMEM supplemented with 1% penicillin/streptomycin. The next day, the medium was changed to the standard expansion medium (consisting of 10% FBS-DMEM, 0.1 mM ascorbic acid, 0.5 mg/ml L-glucose, 100 mM HEPES, 1 mM sodium pyruvate, 2 mM L-glutamine and antibiotics) supplemented with or without 50 nM PEDF peptide). The medium was replaced every 3 days for 12 days.

Isolation and Culture of Mesenchymal Stem Cells

Adult 8-wk-old male Sprague-Dawley rats were anesthetized with an intraperitoneal injection of xylazine (10 mg/kg). Femurs were aseptically harvested, washed in a mixture of PBS and antibiotics for 5 minutes, dissected of all soft tissue, transected at their epiphysis, and their marrow cavity was rinsed repeatedly with a mixture of heparin and DMEM. The harvested cells were centrifuged at 1000×g for 10 minutes. Cell pellets were resuspended with DMEM, and then the cell suspension was transferred to a 15-ml centrifuge tube containing 5 ml of Percoll (1.073 g/ml). After centrifugation at 1500×g for 30 minutes, the mononuclear cells in the middle layer were separated, washed three times with PBS and then resuspended in low-glucose DMEM with 10% heat-inactivated FBS and 1% penicillin/streptomycin. Cells were then incubated with 95% air and 5% CO2 at 37° C.; the medium was replaced every 4 days. Unattached cells were discarded and adherent cells were retained. The primary mesenchymal stem cells (MSCs) grew to approximately 80%-90% confluence after culture for 1 week.

For inducing the chondrogenic differentiation of MSCs, $5\times10^5$ expanded MSCs were exposed to chondrogenic medium (high-glucose DMEM with 100 nM dexamethasone, 0.17 mM ascorbic acid-2 phosphate, 10 µg/ml of insulin, 5 µg/ml of transferrin, 5 ng/ml selenium, 1 mM sodium pyruvate, 2 mM L-glutamine, and 2% FBS) supplemented with 10 ng/ml TGF-β2 (R&D Systems; Minneapolis, Minn.). In the PEDF treatment group, cells were cultured in the chondrogenic medium plus 50 nM PEDF peptide. The medium was replaced every other day for 1 week.

Histology

The knee joints were dissected and the surrounding soft tissue was removed. Specimens were fixed in 4% paraformaldehyde and then decalcified with Shandon TBD-2 decalcifier (Thermo Scientific; Logan, Utah). The joints were then sectioned mid-sagittally and embedded in paraffin blocks. Sections (5 µm in thickness) were longitudinally cut.

Before use, fixed samples were de-pa raffinized in xylene and rehydrated in a graded series of ethanol. The sample were then stained with hematoxylin and eosin (H&E) or used for immunohistochemical examination. 20 sections per knee were carefully prepared so as to include the most severely degenerated area.

Immunofluorescence and BrdU Staining

Paraffin-embedded joint specimens were deparaffinized in xylene and rehydrated in a graded series of ethanol. Deparaffinized specimens were then exposed to 1 N HCl at room temperature for 1 hour for subsequent immunofluorescence study.

For immunofluorescence study, the specimens were blocked with 10% goat serum and 5% BSA for 1 hour. Immunostaining was done using primary antibodies against aggrecan (1:100 dilution), type II collagen (1:100 dilution), and BrdU (1:100 dilution) at 37° C. for 2 hours, followed by incubation with the appropriate rhodamine- or FITC-conjugated donkey IgG for 1 hour at room temperature. Nuclei were located by counterstaining with Hoechst 33258 for 7 min. Images were captured using a Zeiss epifluorescence microscope with a CCD camera. Blinded quantification was performed in triplicate by manually counting cells from 20 randomly-selected fields in each section.

RNA Extraction and Reverse Transcription-Polymerase Chain Reaction (RT-PCR)

The total RNA was extracted from cells using the TRIzol and treated with RNase-free DNase I (Qiagen, Santa Clarita, Calif.) to remove genomic DNA and then purified with an RNA purification kit (Dynabeads). 1 µg of total RNA retrieved from BM-MSCs was reverse-transcribed into cDNA by 200 units of expand Reverse-Transcriptase (Roche, Mannheim, Germany) in 20 µl of reaction buffer containing 0.25 µg of random primers and 0.8 mM dNTPs at 42° C. for 1 hour.

2 µl of the cDNA was used for the PCR reaction as templates. PCR was performed in a 30 µl volume containing 15 µl of EconoTaq® PLUS GREEN 2× Master Mix (Lucigen® Corp.), 1 µM of each primer and 2 µl of template DNA. cDNA was synthesized in an 18-22 cycle amplification reaction (denaturation, 20 s, 94° C.; annealing, 30 s, 57° C.; and polymerization, 40 s, 72° C.). The number of cycles for the primer set was chosen to be in the linear range of amplification. The sequences of specific PCR primers were rat aggrecan (accession number: J03485) sense, TTGGAAATCCAGAACCTTCG (SEQ ID NO: 12); antisense, GTCCAGTGTGTAGCGTGTGG (SEQ ID NO: 13); PCR product: 149 bp; and rat glyceraldehyde 3-phosphate dehydrogenase (GAPDH; accession number: X02231.1) sense, AGACAGCCGCATCTTCTTGT (SEQ ID NO: 14); antisense, CTTGCCGTGGGTAGAGTCAT (SEQ ID NO: 15); PCR product: 207 bp. The PCR products were electrophoresed in a 2% agarose gel containing ethidium bromide and visualized by UV illumination. The intensities of the PCR products were quantified densitometrically using a FUJI LAS-3000 system and Multi Gauge Ver. 1.01 software (Fujifilm, Tokyo, Japan).

Statistics

Results were expressed as the mean±standard error of the mean (SEM). One-way ANOVA was used for statistical comparisons. P<0.05 was considered significant, unless otherwise specified.

Example 1

PEDF Peptides Stimulates Chondrocyte Proliferation and Cartilage Regeneration In Vivo Knee osteoarthritis is a common chronic degenerative disease characterized by loss of articular cartilage. Injection of mono-iodoacetate (MIA), an inhibitor of glycolysis, into the femorotibial joint space of rodents has been reported to induce loss of articular cartilage similar to that noted in human OA. It has been established that extensive chondrocyte degeneration/necrosis usually arises at 7 days after MIA injection. Therefore, PEDF peptide treatment was started on day 8 post-MIA injection, so as to elucidate whether the present PEDF peptides promote cartilage regeneration.

Rats were randomly assigned to 6 experimental groups (n=6, each group) and treated as follows. In the HA group, rats received 25 µl of 5% hyaluronic acid injection. In the Vehicle/HA group, rats were treated with DMSO vehicle re-dissolved in 25 µl of 5% HA. As to the 29-mer/HA, 24-mer/HA, 20-mer/HA, and 18-mer/HA groups, rats received 0.2 mM PEDF peptide (29-mer, 24-mer, 20-mer or 18-mer) re-dissolved in 25 µl of 5% HA. Treatments were applied by way of a single intra-articular injection once on day-8, 12, 16 and 20, respectively, post-MIA injection.

Joint specimens were obtained on day-18 and day-25 post-MIA injection, and representative images of H&E stained sections are provided in FIG. 1. By comparing with the normal joint that were not subjected to MIA injection, morphological changes associated with osteoarthritis (including the reduction of cartilage, the superficial fibrosis of cartilage and subchondral bone collapse) is noted in Vehicle/HA and 18-mer/HA groups, especially at weight bearing sites. In contrast, in specimens from the 20-mer/HA group, the cartilage surface is smoother and the cartilage and subchondral bone are relatively integral, as compared with those in the Vehicle/HA and 18-mer/HA groups. Other PEDF peptides such as 29-mer and 24-mer exhibit similar effects to the 20-mer (data not shown). These findings indicate that the pathological changes associated with osteoarthritis may be abolished by the present PEDF peptides.

Normal cartilage has an organized layered structure that can be functionally and structurally divided into three zones: the superficial zone, the middle (or transitional) zone, and the radial/deep zone. The superficial zone is the articulating surface that provides a smooth gliding surface; this zone makes up approximately 10% to 20% of articular cartilage thickness. Chondrocytes in the superficial zone are characterized by an elongated, spindle appearance, and collagen fibers in this zone have a highly ordered alignment parallel to the articular surface. The transitional zone encompasses 40% to 60% of the articular cartilage volume. This zone has less organized arrangement of the collagen fibers, and chondrocytes in this layer are more rounded than in the superficial layer. The deep zone makes up 30% of the cartilage and consists of large diameter collagen fibrils oriented perpendicular to the articular surface. The chondrocytes are typically arranged in columnar fashion parallel to the collagen fibers and perpendicular to the joint line. Representative microscopic images illustrating the layered structure are provide in FIG. 2, in which the images were taken from knee specimens obtained on 25 days after MIA injection.

Figure 2:
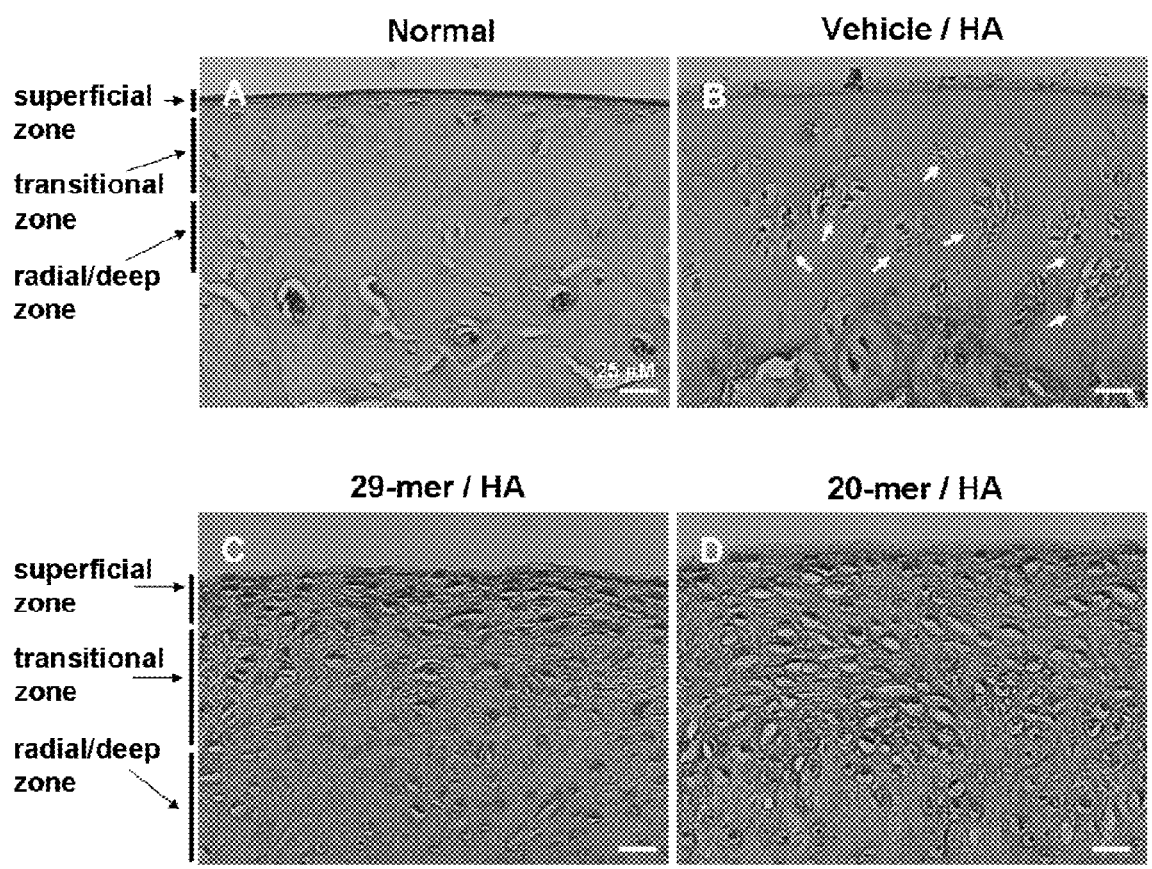
FIG. 2 provides representative microscopic images of knee joint tissue sections from the working example of FIG. 1 (original magnification, ×400)

As could be seen in FIG. 2, the normal cartilage was hypocellular; whereas in knees treated with vehicle/HA, extensive chondrocytes were lost from the superficial zone, and scattered cell cloning (indicated by arrow) occurred in the transitional zone and radial zone. By contrast, the 29-mer/HA and 20-mer/HA treatments lead to the occupation of large numbers of newly generated chondrocyte throughout the cartilage. In addition, in knees treated with the present PEDF peptides, chondrocytes were more organized in each layer. This finding suggests that a cartilage regeneration process, composed of chondrocyte proliferation and structure reorganization, is initiated by the present PEDF peptides.

Figure 3:
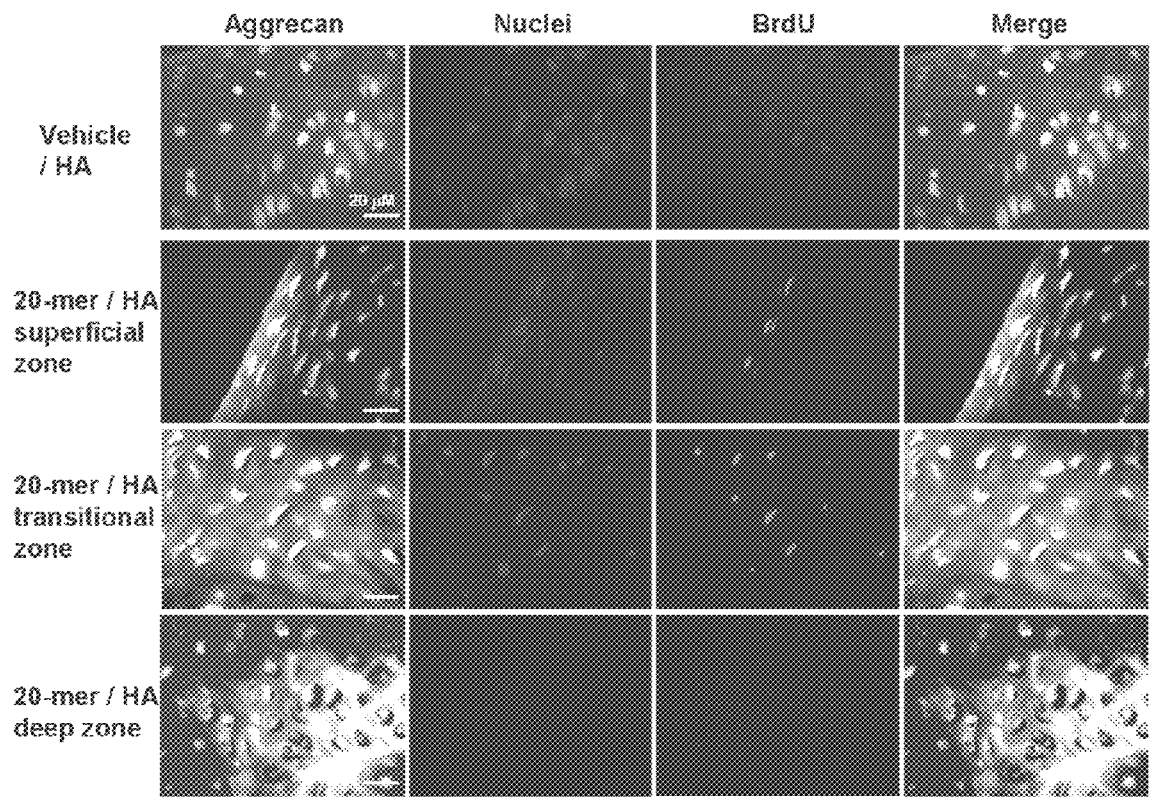
FIG. 3 provides representative immunostained images of knee joint specimens according to another working example of the present disclosure (original magnification, ×1000)

Osteoarthritis causes loss of extracellular matrix (ECM), such as aggrecan and type II collagen, in the degenerated cartilage. As illustrated in FIG. 3 (left panels), the aggrecan-positive signals (green) were heavily accumulated in superficial, transitional and deep zone of cartilage from knees treated with 20-mer, but had faint staining in cartilage from the vehicle-treated knee. Immunohistochemical analysis of knee sections using anti-type 2 collagen antibody showed the similar restoration of ECM by the present PEDF peptides (data not shown), supporting the notion that the present PEDF peptides promote cartilage repair. In addition, the population of chondrocytes, as indicated by aggrecan staining, was much higher in 20-mer-treated cartilage as comparing to the vehicle-treated cartilage.

Dual-immunofluorescent staining for aggrecan and nucleus (stained blue with Hoechst 33258; FIG. 3 middle panels) indicated that over 95% of cells were aggrecan-positive cells in the 20-mer/HA group, suggesting that the present PEDF peptides may promote cartilage healing by triggering chondrocyte proliferation.

Further, immunohistochemical analysis by anti-BrdU antibody revealed that the numbers of BrdU-positive cells in the 20-mer/HA group increased significantly, as compared with those in the vehicle/HA group (FIG. 3, right panels). Quantitative analysis was performed as described above from 3 sections per knee joint specimen, and 6 rats at each group. The BrdU/aggrecan labeling index (%) was computed as the number of BrdU- and aggrecan-double positive cells divided by the total number of aggrecan-positive cells. Results are summarized in Table 1; *$P<0.0001$ versus the vehicle/HA group.

TABLE 1

| Treatment | BrdU/Aggrecan Labeling Index (%) |
|---|---|
| Vehicle/HA | 0.5 ± 0.34 |
| 29-mer/HA | 15.0 ± 2.38* |
| 24-mer/HA | 16.0 ± 2.03* |
| 20-mer/HA | 17.5 ± 2.7* |
| 18-mer/HA | 0.67 ± 0.33 |
| HA | 0.71 ± 0.28 |

Data in Table 1 indicates that the treatment of the present PEDF peptides (e.g., 29-mer, 24-mer and 20-mer) promotes chondrocyte proliferation, as compared to the treatment of HA or vehicle/HA. It is also noted that the 18-mer which does not comprise the "SLGA residues," does not elicit such promoting effect.

In conclusion, the results in Example 1 reveal that the present PEDF peptides are effective in promoting the chondrocyte proliferation in damaged cartilage, which is the fundamental mechanism for cartilage regeneration. Therefore, it is believed that cartilage regeneration may be enhanced by the present PEDF peptides.

Example 2

PEDF Peptides Promotes Articular Chondrocyte Proliferation In Vitro

Primary chondrocytes were isolated from rat articular cartilage and cultivated in the presence or absence of the present PEDF peptides to elucidate the stimulating effect of the present PEDF peptides on chondrocyte proliferation.

Figure 4:
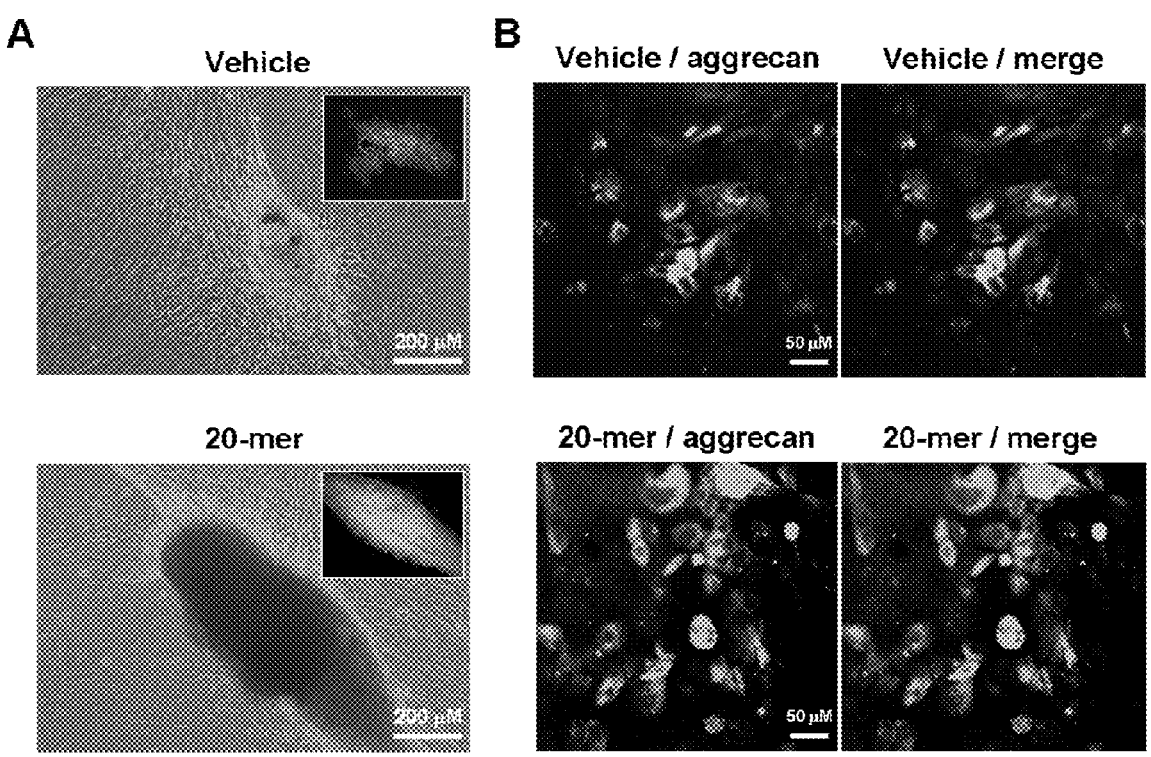
FIG. 4A provides representative images illustrating the morphology of articular cartilage-derived colony and immunostained image of the colony to exhibit the identity thereof, according to another working example of the present disclosure.
FIG. 4B provides representative immunostained images of cells from rat articular cartilage according to the working example of FIG. 4A (original magnification, ×1000).

The photographs in FIG. 4A reveal that in the presence of the present PEDF peptide (e.g., 20-mer), chondrocytes grew faster and aggregated into huge three dimensional colonies. By contrast, in the vehicle group, the colonies are much smaller in the absence of PEDF peptides. The chondrocyte identity of cells within the colony was confirmed by aggrecan immunostaining (FIG. 4A, inserts). The level of aggrecan-positive cells in the monolayer culture (FIG. 4B) were quantified from 20 randomly selected fields, and the aggrecan labeling index (%) was computed as the number of aggrecan-labeled cells divided by the total number of cells (nucleus labeling by Hoechst 33258). Results are summarized in Table 2; *$P<0.01$ versus untreated cells.

TABLE 2

| Treatment | Aggrecan Labeling Index (%) |
|---|---|
| Untreated | 32.3 ± 3.7 |
| 29-mer | 52.2 ± 5.2* |
| 24-mer | 50.0 ± 2.9* |
| 20-mer | 50.1 ± 3.6* |
| 18-mer | 31.8 ± 2.6 |

In sum, the present PEDF peptides (e.g., the 29-mer, 24-mer, and 20-mer) promote chondrocyte expansion in culture; this finding supports the conclusion that these PEDF peptides stimulate chondrocyte proliferation in vivo. The enhanced aggrecan production in cultured chondrocytes also reflects the regeneration of cartilage matrix in vivo.

Example 3

PEDF Peptides Promote Chondrogenesis of Mesenchymal Stem Cells

Mesenchymal stem cells (MSCs) have been advocated as chondrogenic cell source for cartilage repair. This examples aims to investigate whether the present PEDF peptides enhance the chondrogenic differentiation of MSCs in culture.

MSCs were isolated and cultured as described in the "Materials and Methods" section above. The expression level of aggrecan mRNA was quantified by RT-PCR analysis, and results are normalized with the expression level of GAPDH gene. The fold of induction with respect to the vehicle group (set to 1) are summarized in Table 3; *$P<0.0002$ versus the vehicle group.

TABLE 3

| Treatment | Induction fold |
| --- | --- |
| Expansion medium | 0 |
| Vehicle | 1 |
| 29-mer | 3.8 ± 0.35* |
| 24-mer | 3.7 ± 0.56* |
| 20-mer | 3.5 ± 0.34* |
| 18-mer | 1.1 ± 0.13 |

As could be seen in Table 3, aggrecan mRNA was barely detectable in MSCs cultivated in expansion medium. By contrast, MSCs that were cultivated in the chondrogenic medium (the vehicle group) would differentiate into chondrocytes, as evident from substantial expression of aggrecan mRNA. Exposure of cells to the present PEDF peptides (29-mer, 24-mer and 20-mer) induced at least a 3.5-fold increases of aggrecan mRNA, as compared with that of the vehicle group. Also, the treatment with the 18-mer (i.e., the synthetic peptide that does not have the "SLGA" residues) had no effect in promoting the chondrogenic differentiation.

Immunostaining for aggrecan and type II collagen was also performed to investigate the pro-differentiation activity of the present PEDF peptides. The level of aggrecan-positive cells were quantified from 20 randomly selected fields, and the aggrecan labeling index (%) was computed as the number of aggrecan-labeled cells divided by the total number of cells (nucleus labeling by Hoechst 33258). Results are summarized in Table 4; *$P<0.0001$ versus the vehicle group.

TABLE 4

| Treatment | Aggrecan Labeling Index (%) |
| --- | --- |
| Vehicle | 33.8 ± 3.9 |
| 29-mer | 76.8 ± 5.0* |
| 24-mer | 78.8 ± 4.3* |
| 20-mer | 78.7 ± 3.8* |
| 18-mer | 34.2 ± 3.8 |

Results in Table 4 indicate that in the presence of the present PEDF peptides (e.g., 29-mer, 24-mer, and 20-mer), more cells differentiated towards chondrocytes, as compared with those of the vehicle group. By contrast, the 18-mer fails to provide such enhancement of differentiation efficiency of BM-MSCs into chondrocytes. In summary, these findings reveal that the present PEDF peptides promote the chondrogenic differentiation of MSCs.

The present disclosure is the first to demonstrate that short, synthetic PEDF peptides have protective effect against cartilage damages caused by osteoarthritis. As compared with the conventional delivery of vectors expressing full-length PEDF peptides, the application of such short, synthetic PEDF peptides is a safe and less expensive approach.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating osteoarthritis in a subject, comprising: administering to the subject at a site in need of treatment a synthetic peptide consisting of an amino acid sequence having 20-39 amino acid residues in length, wherein the amino acid sequence at least includes a sequence selected from the group consisting of SEQ ID NOs: 1-3, 5, 6, 8, and 9.

2. The method of claim 1, wherein 4 consecutive residues of the synthetic peptide are identical to residues 11-14 of SEQ ID NO: 1.

3. The method of claim 1, wherein the subject is a human.

4. The method of claim 1, wherein the synthetic peptide is formulated into a pharmaceutical composition comprising,
an effective amount of the synthetic peptide; and
a pharmaceutically acceptable excipient.

5. The method of claim 4, wherein 4 consecutive residues of the synthetic peptide are identical to residues 11-14 of SEQ ID NO: 1.

6. The method of claim 4, wherein the subject is a human.

7. The method of claim 4, further comprising a glycosaminoglycan.

8. The method of claim 7, wherein the glycosaminoglycan is hyaluronic acid or sodium hyaluronate.

9. The method of claim 4, wherein the pharmaceutical composition is in the form of a solution, gel, semi-solid, or solid.

10. The method of claim 1, wherein the administering is by introducing the synthetic peptide into a synovial cavity of the subject.

11. The method of claim 10, wherein 4 consecutive residues of the synthetic peptide are identical to residues 11-14 of SEQ ID NO: 1.

12. The method of claim 10, wherein the subject is a human.

13. The method of claim 10, wherein the synthetic peptide is formulated into a pharmaceutical composition comprising the synthetic peptide and a pharmaceutically acceptable excipient.

14. The method of claim 13, wherein the pharmaceutical composition further comprises a glycosaminoglycan.

15. The method of claim 14, wherein the glycosaminoglycan is hyaluronic acid or sodium hyaluronate.

16. The method of claim 13, wherein the pharmaceutical composition is in the form of a solution, gel, semi-solid, or solid.

17. The method of claim 10, wherein the synthetic peptide is intra-articularly injected into the synovial cavity.

* * * * *